US008114420B2

(12) United States Patent
Xia et al.

(10) Patent No.: US 8,114,420 B2
(45) Date of Patent: *Feb. 14, 2012

(54) COMPOSITION FOR TREATING DRY EYE AND RELATED METHODS OF MANUFACTURE AND METHODS OF USE

(75) Inventors: Erning Xia, Penfield, NY (US); Joseph Salamone, Boca Raton, FL (US); X. Michael Liu, Penfield, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 575 days.

This patent is subject to a terminal disclaimer.

(21) Appl. No.: 11/391,056

(22) Filed: Mar. 28, 2006

(65) Prior Publication Data
US 2006/0222623 A1 Oct. 5, 2006

Related U.S. Application Data

(60) Provisional application No. 60/666,843, filed on Mar. 31, 2005.

(51) Int. Cl.
*A61K 9/00* (2006.01)
(52) U.S. Cl. ........................................ 424/400
(58) Field of Classification Search .................. 424/400
See application file for complete search history.

(56) References Cited

U.S. PATENT DOCUMENTS

| 2,703,777 | A | * | 3/1955 | Feinstein et al. ............. 424/642 |
| 4,409,205 | A | * | 10/1983 | Shively ..................... 424/78.04 |
| 5,106,615 | A | * | 4/1992 | Dikstein ..................... 424/78.04 |
| 5,209,927 | A | | 5/1993 | Gressel et al. |
| 5,294,607 | A | | 3/1994 | Glonek et al. |
| 5,679,665 | A | * | 10/1997 | Bergamini et al. ........... 514/171 |
| 5,800,807 | A | * | 9/1998 | Hu et al. ..................... 424/78.04 |
| 6,353,022 | B1 | | 3/2002 | Schneider et al. |
| 6,806,364 | B2 | * | 10/2004 | Su et al. ........................... 536/43 |
| 2002/0107238 | A1 | | 8/2002 | Bandyopadhyay et al. |
| 2004/0192647 | A1 | * | 9/2004 | Babizhayev ................... 514/57 |

FOREIGN PATENT DOCUMENTS

| EP | 592348 | 1/1998 |
| EP | 538313 | 4/1999 |
| JP | 05000951 | 1/1993 |
| WO | WO 2006/055454 A2 | 5/2006 |

OTHER PUBLICATIONS

Patton T.F. et al., Ocular Evaluation of Polyvinyl Alcohol Vehicle in Rabbits, 1975, J Pharm Sci, vol. 64, pp. 1312-1316.*
Adler C.A. et al., The effect of Viscosity of the Vehicle on the Penetration of Fluorescein into the Human Eye, 1971, Exp Eye Research, vol. 11, pp. 34-42.*

(Continued)

*Primary Examiner* — Sreeni Padmanabhan
*Assistant Examiner* — Gigi Huang
(74) *Attorney, Agent, or Firm* — Toan P. Vo

(57) ABSTRACT

The present invention is directed to a composition for treating dry eye comprising, in one embodiment, carboxymethylcellulose and a polyol. Such compositions have been found to alleviate the symptoms of dry eye and remain in the eye for a long period of time.

5 Claims, 2 Drawing Sheets

Typical chromatograms of CMC using aqueous SEC with triple detection (Neat CMC-MV)

OTHER PUBLICATIONS

Goswamy, Glycerine eye drops in keratopathy, 1983, Indian J Ophthalmol, 31:389-390, printed from http://www.ijo.in/printarticle.asp?issn=0301-4738;year=1983;volume=31;issue=4;spage=389;epage=390;aulast=Goswamy, printed on Sep. 10, 2008, 2 pages.*

Hercules Incorporated, Aqualon-Sodium Carboxymethylcellulose Chemistry, 2000, printed from http://www.herc.com/aqualon/product_data/aq_bro_cmc_chem.html, 2 pages.*

Sperling, "Intrinsic Viscosity," Introduction to Physical Polymer Science, 3 ed., John Wiley & Sons, Inc., 2001, p. 96-103.

* cited by examiner

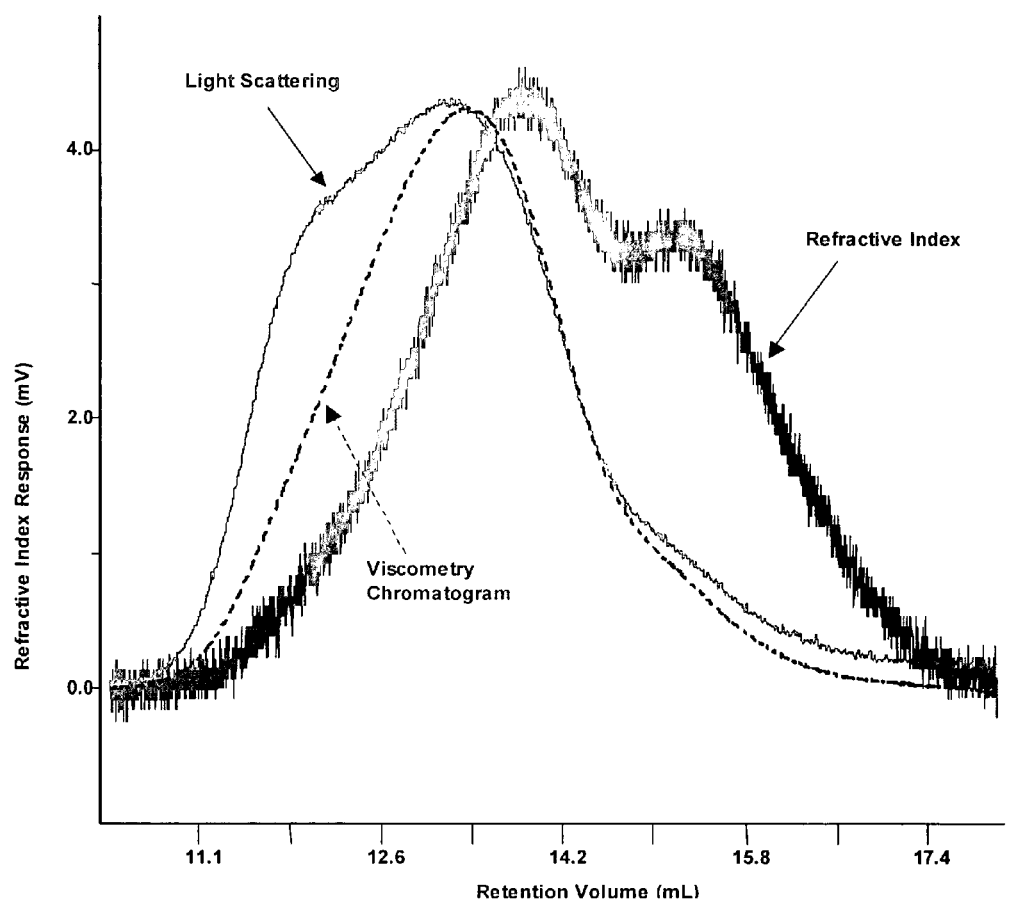
Figure 1. Typical chromatograms of CMC using aqueous SEC with triple detection (Neat CMC-MV)

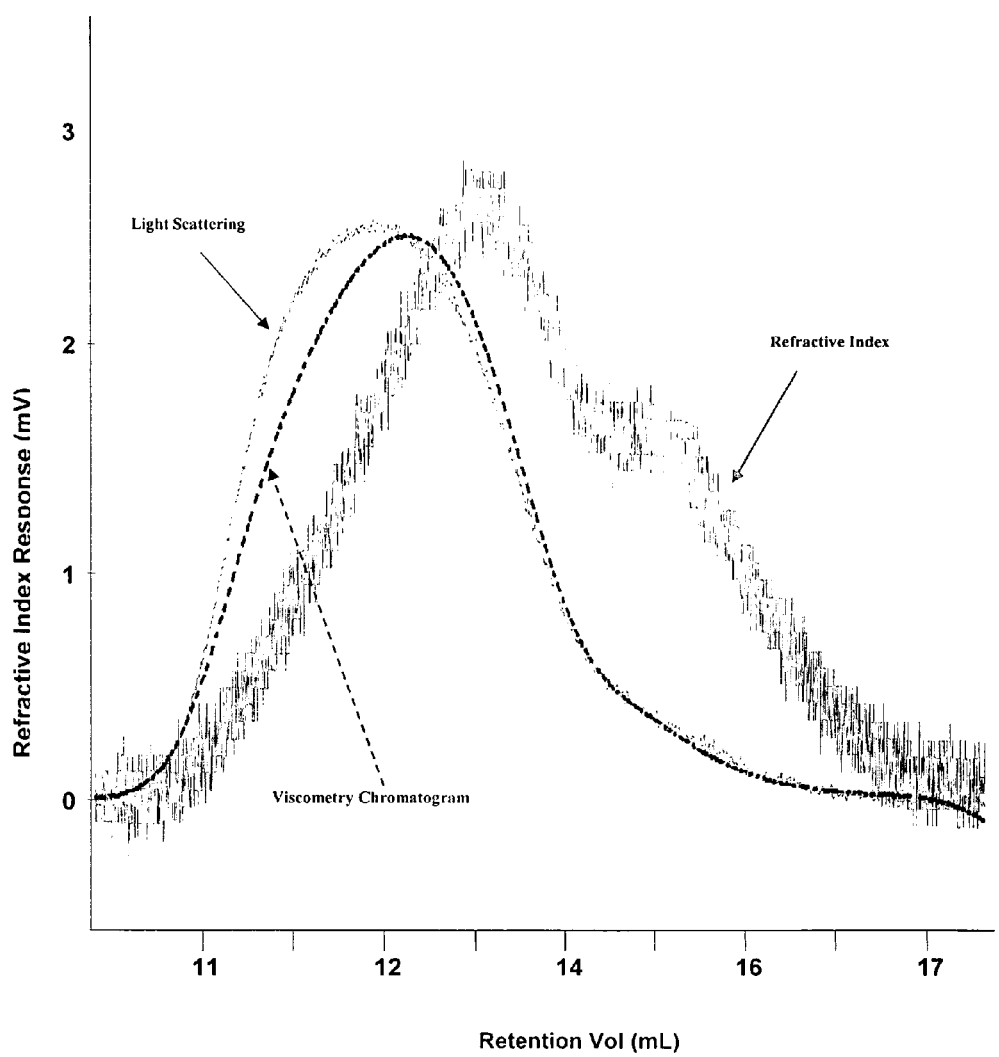
Figure 2. Typical chromatograms of CMC with Glycerin using aqueous SEC with triple detection (Formulation-8)

COMPOSITION FOR TREATING DRY EYE AND RELATED METHODS OF MANUFACTURE AND METHODS OF USE

CROSS-REFERENCE

This application claims the benefit of Provisional Patent Application No. 60/666,843 filed Mar. 31, 2005 and is incorporated herein by reference.

FIELD OF THE INVENTION

This invention relates to a composition for treating dry eye and a related method of use and method of manufacture. In particular, the invention relates to a method of treating dry eye without a pharmaceutical agent.

BACKGROUND

Dry eye, also known generically as keratoconjunctivitis sicca and dyslacrima, is a common ophthalmological disorder affecting millions of people. A patient with dry eye may experience burning, a feeling of dryness and persistent irritation. In severe cases, dry eye can seriously impair a person's vision and hence handicap the sufferer in activities such as driving. Certain diseases such as Sjogren's disease manifest dry eye symptoms. Also, as people age, the lacrimal glands in the eye may produce less moisture, resulting in eyes that become dry, inflamed, itchy and gritty.

Although it appears that dry eye may result from a variety of underlying, unrelated pathogenic causes, all presentations of the condition share a common effect, namely the breakdown of the pre-ocular tear film, which commonly results in dehydration of the exposed outer surface and hence the symptoms described above.

A number of approaches exist for the treatment of dry eye. One common approach has been to supplement the ocular tear film using artificial tears instilled throughout the day. Examples of the tear substitute approach include the use of buffered, isotonic saline solutions and aqueous solutions containing water-soluble polymers that render the solutions more viscous and thus less easily shed by the eye by the washing action of the tear fluid. See, for example, U.S. Pat. No. 5,209,927 to Gressel, et al.; U.S. Pat. No. 5,294,607 to Glonek, et al.; and U.S. Pat. No. 4,409,205 to Shively;

Although these approaches have met with some success in some cases, significant challenges in the treatment of dry eye nevertheless remain. Problems include the fact that the use of tear substitutes, while temporarily effective, generally require repeated application over the course of a patient's waking hours, not uncommonly ten to twenty times over the course of a day. Such an approach is not only inconvenient and time consuming, but not very effective in preventing at least the initiation of dry-eye symptoms. Although increasing the viscosity of the dry-eye product may extend the product's duration in the eye or increase in viscosity is effective at extending duration only to a limited extent. Viscous ophthalmic drops are sometimes undesirable because they feel sticky in the eye. Further, increases in the duration of the product would be highly desirable. Carboxymethylcellulose (CMC) is a known viscosifier and demulcent in ophthalmic formulations including formulations for the delivery of a pharmaceutical agent. Polyols including glycerin are known as demulcents and hypotonicity adjusting agents in ophthalmic formulations including formulations for the delivery of a pharmaceutical agent. See EP Publ. No. 538,313 and EP Publ. 592,348 that teach selection of one of several ingredients including carboxymethylcellulose and one of several ingredients including glycerin.

JP Abstract No. 05000951 teaches a drug delivery composition comprising a corticosteroid delivered in a suspending agent (e.g. carboxymethylcellulose sodium and methylcellulose and a suspending assistant (e.g. concentrated glycerol, propylene glycol, glucose or lactose).

In view of the above, it would be desirable to provide an eye-drop solution that is optimized in its ability to last longer in the eye and/or will better alleviate the symptoms of dry eye. An ophthalmic dry eye solution that is safe, convenient and economical to use is also desireable. In particular, it would be highly desirable to develop a product having significantly greater duration of efficacy, in order to significantly decrease the number of times that the product may need to be administered to the eye, over the course of a day, in order to effectively treat the symptoms of dry eye. The present invention addresses some or all of these and/or other needs.

U.S. Pat. No. 5,106,615 discloses the combination of a polyol with a carbomer polymer the invention is a long-lasting dry eye formula.

SUMMARY OF THE INVENTION

The present invention is a dry eye composition comprising an aqueous solution of carboxy-containing polymer and a polyol wherein the carboxy-containing polymer has a molecular weight that is a minimum of about 90 kDa and a maximum of about 700 kDa and has a Mark-Houwink constant that is a minimum of about 0.6 and a maximum of about 1.5. In one embodiment, the polyol is poly(ethylene glycol) or glycerin.

In another embodiment the polysaccharide is selected from the group comprising carboxy-containing cellulose, hyaluronate, chondroitin sulfate, guar, alginate, carbomers, pectin and xanthan. Preferably, the carboxy-containing polysaccharide is carboxyethyl cellulose.

In another embodiment, there is a method of treating dry eye comprising administering to an eye a composition comprising an aqueous solution of carboxymethylcellulose and a polyol to the eye.

In still another embodiment, there is a method of manufacturing a dry eye composition comprising combining in an aqueous solution ophthalmically pure carboxy-containing polymer with ophthalmically pure polyol, wherein the carboxy-containing polymer has a molecular weight that is a minimum of about 90 kDa and a maximum of about 700 kDa and has a Mark-Houwink constant that is a minimum of about 0.6 and a maximum of about 1.5.

BRIEF DESCRIPTION OF THE DRAWINGS

The objects, features and advantages of the various embodiments of the present invention will become more readily apparent from the following detailed description together with the following drawings.

FIG. 1 is a triple detection size exclusion chromatography graphic representation of a formulation of carboxymethylcellulose in water.

FIG. 2 is a triple detection size exclusion chromatography graphic representation of a formulation of carboxymethylcellulose and glycerin in water.

DETAILED DESCRIPTION OF THE INVENTION

The present invention is directed to a dry eye composition comprising an aqueous solution of carboxy-containing polymer and a polyol wherein the carboxy-containing polymer has a molecular weight that is a minimum of about 90 kDa and a maximum of about 700 kDa and has a Mark Houwink-Number that is a minimum of about 0.6 and/or a maximum of about 1.5. The composition has been shown to moisturize the eye for a relatively long duration.

The polyol of the present invention is typically a polyol containing 2 to 6 carbon atoms. Preferably, The polyol contains 2 to 4 carbon atoms. The polyol of one embodiment is selected from the group consisting of glycerin, ethylene glycol, poly(ethylene glycol), propylene glycol, sorbitol, manitol and monosaccharides, disaccharides and oligosaccharides. In one preferred embodiment, the polyol is selected from the group consisting of glycerin, ethylene glycol, propylene glycol, sorbitol, mannitol and monosaccharides. In another preferred embodiment, the polyol is selected from the group comprising disaccharides, oligosaccharides and poly(ethylene glycol). In one preferred embodiment, the polyol is glycerin.

The concentration of polyol including glycerin is a minimum of about 0.01 wt. % about 0.05 wt. % about 0.1 wt. % or about 0.5 wt. % and/or a maximum of about 1.0 wt. %, about 1.5 wt. %, about 2.0 wt. %, about 3.0 wt. % or about 4.0 wt. % based upon the total weight of the composition.

In an embodiment, the carboxy-containing polymer is a carboxy-containing polysaccharide. Suitable polysaccharides of the present invention include carboxy-containing polysaccharides selected from the group consisting of carboxy-containing cellulose, hyaluronate, chondroitin sulfate, alginate, carbomers, pectin and xanthan.

The present invention of one embodiment includes carboxymethylcellulose and alginate.

In one embodiment, the average molecular weight of carboxy-containing polymer is a minimum of about 90 kDa and a maximum of about 700 kDa. Generally, the average molecular weight of the carboxy-containing polymer is a minimum of about 150 kDa, about 200 kDa or about 250 kDa. The average molecular weight of the carboxy-containing polymer is a maximum of about 650 kDa, about 600 kDa, about 550 kDa or about 500 kDa.

The concentration of carboxy-containing polymer is a minimum of about 0.01 wt. % and a maximum of about 2.0 wt. % based upon the total weight of the solution. Typically, the concentration of carboxy-containing polymer is a minimum of about 0.05 wt. %, 0.1 wt. %, 0.5 wt. % or about 1 wt. % based upon the total weight of the solution. Typically, the concentration of carboxy-containing polymer is a maximum is about 1.75 wt. %, 1.5 wt. % and 1.2 wt. % based upon the total weight of the solution. Preferably, the concentration of carboxy-containing polymer is about 1.0 wt. % based upon the total weight of the solution.

It is likewise preferable if the carboxy-containing polymer has a degree of substitution value that is a minimum of about 0.5 and a maximum of about 1.5. Typically, the carboxy-containing polymer has a degree of substitution value that is a minimum of about 0.25, about 0.5 or about 0.6 and/or a maximum of about 0.6, about 0.7, about 0.8 about 0.9 or about 1.0.

According to one embodiment, the ratio of carboxy-containing polymer to polyol is a minimum of about 1:4, about 1:3, about 1:2, about 2:3 or about 3:4 and/or a maximum of about 4:1, about 3:1, about 2:1, about 3:2 or about 4:3.

The present composition may also contain a disinfecting amount or a preservative of an antimicrobial agent. Antimicrobial agents are defined as organic chemicals that derive their antimicrobial activity through a chemical or physiochemical interaction with the microbial organisms. These include sorbic acid, quarternary ammonium polymers and low and high molecular weight biguanides. For example, biguanides include the free bases or salts of alexidine, chlorhexidine, hexamethylene biguanides and their polymers, and combinations of the foregoing. The salts of alexidine and chlorhexidine can be either organic or inorganic and are typically gluconates, nitrates, acetates, phosphates, sulfates, halides and the like. A preferred polymeric biguanide is poly (hexamethylene biguanide) commercially available from Zeneca, Wilmington, Del. under the trademark Cosmocil™ CQ. Generally, the hexamethylene biguanide polymers, also referred to as poly(aminopropyl biguanide) (PAPB), have molecular weights of up to about 100 kDa. A particularly preferred preservative is alexidine.

If used in the subject solution, the antimicrobial agent should be used in an amount which will preserve or prevent the growth of the microorganism population in the formulations employed. Preferably, a preservative amount is that which will reduce the bacterial bioburden after 28 days each by 3 logs and prevents the growth of fungal bioburden by ±0.5 log. Typically, such agents are present in a minimum concentration of about 0.0001 wt. %, 0.0003 wt. % or 0.0005 wt. % and a maximum concentration of about 0.0005 wt. % or 0.001 wt. % or about 0.005 wt. % based upon the total weight of the composition.

The aqueous solutions employed in this invention may contain additional ingredients described above, one or more other components that are commonly present in ophthalmic solutions, for example, buffers, stabilizers, tonicity agents and the like, which aid in making ophthalmic compositions more comfortable to the user. The aqueous solutions of the present invention are typically adjusted with tonicity agents to approximate the tonicity of normal lacrimal fluids which is equivalent to a 0.9 wt. % solution of sodium chloride or a 2.8 wt. % of glycerol solution. The solutions are made substantially isotonic with physiological saline used alone or in combination; otherwise, if simply blended with sterile water and made hypotonic or made hypertonic, the lenses will lose their desirable optical parameters. Correspondingly, excess salt or other tonicity agents may result in the formation of a hypertonic solution that will cause stinging and eye irritation. An osmolality is a minimum of about 200 mOsm/kg, about 225 mOsm/kg, about 250 mOsm/kg, about 260 mOsm/kg, about 280 mOsm/kg, about 300 mOsm/kg or about 320 mOsm/kg and/or a maximum of about 400 mOsm/kg, about 380 mOsm/kg, about 360 mOsm/kg, about 340 mOsm/kg or about 320 mOsm/kg. Most preferably, the osmolality is about 240 mOsm/kg to about 320 mOsm/kg.

Preferably, the composition of at least one embodiment of the present invention has a low ionic strength. Typically, the composition contains low concentration of mono or divalent cations typically found in tear fluids. Generally, the composition contains a low concentration of one or more of the following cations: Na+, K+, Ca++, Mg++, and Zn++. In one embodiment, the concentration of the mono or divalent cations that are typically found in tear fluids (i.e. Na+, K+, Ca++, Mg++ and Zn++) has a minimum concentration of about 0.001 wt. %, about 0.005 wt. %, about 0.01 wt. % or about 0.1 wt. % and/or a maximum of about 0.1 wt. %, about 0.05 wt. % or about 0.01 wt. % based upon the total weight of the composition.

The pH of the present solutions used to treat dry eye should be maintained at a minimum of about 4 about 5, about 5.5, about 6, about 6.5 and/or a maximum of about 7.5, about 7.8, about 8, about 8.5. Suitable buffers may be added, such as borate, citrate, bicarbonate, aminoalcohol buffers, MOPS buffer, bicine, tricine, TRIS, BIS/TRIS and various mixed phosphate buffers (including combinations of $Na_2HPO_4$, $NaH_2PO_4$ and $KH_2PO_4$) and mixtures thereof. Borate buffers are preferred, particularly for enhancing the efficacy of PAPB. Preferred combination buffers include borate/phosphate and borate/citrate combination buffers. Generally, buffers will be used in amounts having a minimum of about 0.05 wt. % or about 0.1 wt. % and/or a maximum of about 1.5 wt. % or about 2.5 wt. %.

In addition to buffering agents, in some instances it may be desirable to include sequestering agents in the present solutions in order to bind metal ions, which might otherwise react with the lens and/or protein deposits and collect on the lens. Ethylene-diaminetetraacetic acid (EDTA) and its salts (disodium) are preferred examples. They are usually added in amounts having a minimum of about 0.01 wt. % and/or a maximum of about 0.2 wt. %.

The present invention includes a method of treating dry eye comprising administering to an eye a composition comprising an aqueous solution of carboxymethylcellulose and a polyol to the eye. In one embodiment the composition does not have a active pharmaceutical agent. The method further includes administering to an eye a composition to any one or more embodiments or combination of embodiments disclosed herein.

In one embodiment, there is a method of manufacturing a dry eye composition. The method of manufacturing comprises combining in an aqueous solution ophthalmically pure carboxymethylcellulose (eg. sodium carboxymethylcellulose) without adding a active pharmaceutical agent. The carboxymethylcellulose has a molecular weight that is a minimum of about 90 kDa and a maximum of about 700 kDa with ophthalmically pure polyol.

As indicated above, the present invention is useful for treating dry eye, or, more specifically, its symptoms. For that purpose, compositions for use in the present invention may be sold in a wide range of small-volume containers from 1 ml to 30 ml in size. Such containers can be made from HDPE (high density polyethylene), LDPE (low density polyethylene), polypropylene, poly(ethylene terepthalate) and the like. Flexible bottles having conventional eye-drop dispensing tops are especially suitable for use with the present invention.

The above-described solutions, in accordance with the present invention, may be used by instilling, for example, about one (1) or three (3) drops in the affected eye(s) as needed, for the temporary relief of burning and irritation due to dryness in the eye and for use as a protectant against further irritation, or to relieve dryness to the eye.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

Example 1

Effect of Glycerin on Carboxymethylcellulose Physical Structure

Three 1.0 wt. % aqueous solutions of CMC were made and identified as Formulas 1-3. Formula 1 contained only water and 1.0 wt. % carboxymethylcellulose. To Formula 2, 1.0 wt. % glycerin was added. Glycerin was added to Formula 3 in a 3.0 wt. % amount.

Formula 1 was analyzed using size exclusion chromatography (SEC) with triple detection. Particularly, light scattering detection, viscometry trace detection and refractive index detection analysis were performed. The results are shown in FIG. 1. The light scattering curve is shifted more towards the high molecular weight than the viscometry curve. The shift of the light scattering curve and the viscometry curve reflects the increased sensitivity of the light scattering dectector and the viscometry detector to high molecular weight components than the refractive index (RI) detector.

The Mark-Houwink constant (a) is calculated using the technique disclosed in Introduction to Physical Polymer Science, Third Edition, L. H. Sperling, Wiley-Interscience, A John Wiley & Sons, Inc., Publication, New York, 2001. Interpretation of the Mark-Houwink constant is done according to the following Table 1:

TABLE 1

| Values of the Mark-Houwink Constants (a) | |
|---|---|
| Mark-Houwink Constants (a) | Interpretation |
| 0 | Spheres |
| 0.5-0.8 | Random coils |
| 1.0 | Stiff coils |
| 2.0 | Rods |

A Mark-Houwink constant of zero is indicative of a spherical polymeric structure. A Mark-Houwink constant between 0.5 and 0.8 indicates a physical configuration described as random coils. A Mark-Houwink constant above 0.8 indicates a structure that is more ordered than random approaching a stiff coil. A Mark-Houwink constant of about 1.0 is a stiff coil and a Mark-Houwink constant of 2.0 represents a rod-like structure.

Formula 1 representing carboxymethylcellulose with no glycerin had a Mark-Houwink constant of 0.561 as recorded in Table 2. Thus, without glycerin, carboxymethylcellulose formed a random coil.

TABLE 2

| The effect of Solvent Glycerin on the Mark-Houwink Constant of 1.0% Carboxymethylcellulose Solution | | |
|---|---|---|
| Formulation(s) | Glycerin (%) | Mark-Houwink Constant (a) |
| Formula 1 | 0.0% | 0.561 |
| Formula 2 | 1.0% | 0.825 |
| Formula 3 | 3.0% | 0.929 |

Formulation 2 was analyzed using SEC with triple detection. The results are shown in FIG. 2. Both the light scattering curve and the viscometry curve shift towards the higher molecular weight. However, comparing FIG. 1 representing Formula 1 with FIG. 2 representing Formula 2, it becomes apparent that the degree of shift of the light scattering curve in FIG. 2 is similar to the degree of shift of the viscometry curve in FIG. 2. Particularly, the viscometry curve and the light scattering curve in FIG. 2 are closer together than the viscometry curve and the light scattering curve in FIG. 1. The similarity of the shift in the light scattering curve and the viscometry curve results in a Mark-Houwink constant that is higher. Particularly, the Mark-Houwink constant for Formula 2 is 0.825. The carboxymethylcellulose formula with 1.0 wt. % glycerin is outside the range for a random coil and is slightly less than a stiff coil.

Formula 3 was analyzed similar to Formula 2. The Mark-Houwink constant for Formula 3 is 0.929. Thus, a 1.0 wt. % solution of carboxymethylcellulose with a 3 wt. % solution of glycerin has stiff coil properties. It would be expected that the combination of glycerin to carboxymethylcellulose forms ordered coils and in some instances stiff coils. The stiff coil configuration is expected, because of its configuration, to be more difficult to wash out of the eye by tear production and blinking.

Example 2

Effect of Propylene Glycol on Carboxymethylcellulose Physical Structure

Two 1.0 wt. % aqueous solutions of carboxymethylcellulose were made and identified as Formula 4 and Formula 5. Formula 4 contained water, 1.0 wt. % carboxymethylcellulose and 1.0 wt. % propylene glycol. Formula 5 contained water, 1.0 wt. % carboxymethylcellulose and 3.0 wt. % propylene glycol. Formulas 4 and 5 each were analyzed using SEC with lights scattering detection, viscometry trace detection and refractive index detection. Based upon the SEC analysis, a Mark-Houwink constant was calculated and recorded in the following Table 3:

TABLE 3

The effect of Solvent Propylene Glycol on the Mark-Houwink Constant of 1.0% Carboxymethylcellulose Solution

| Formulation(s) | Propylene Glycol (%) | Mark-Houwink Constant (a) |
|---|---|---|
| Formula 4 | 1.0% | 0.725 |
| Formula 5 | 3.0% | 0.926 |

The results show that the addition of propylene glycol likewise resulted in an increase in the Mark-Houwink constant. At 3.0 wt. % of glycerin, the carboxymethylcellulose in solution had properties similar to a stiff coil. The stiff coil properties are expected to result in a dry-eye product that lasts longer in the eye because of the enhanced polymer interactions with ocular tissue.

Example 3

Formulations with Carboxymethylcellulose and Glycerin

Four additional formulations identified in Table 4 were prepared according to the compositions described in Formulas 6-9. Each were analyzed using SEC with light scattering detection, viscometry trace detection and refractive index detection. Based upon the SEC analysis, a Mark-Houwink constant was calculated and recorded in the following Table 4:

TABLE 4

CMC/GLYCEROL FORMULATIONS

| Ingredient/ Properties | Formula 6 % W/W | Formula 7 % W/W | Formula 8 % W/W | Formula 9 % W/W |
|---|---|---|---|---|
| Sodium Borate | 0.215 | 0.115 | 0.065 | 0.120 |
| Boric Acid | 1.000 | 0.500 | 0.500 | 0.500 |
| Trehalose | — | 0.200 | — | — |
| EDTA | 0.050 | 0.050 | 0.050 | — |
| Polymer JR | — | — | 0.010 | — |
| Carboxymethylcellulose | 0.500 | 1.000 | 1.000 | 1.000 |
| Glycerin | 0.500 | 1.000 | 1.000 | 1.000 |
| $ZnCl_2$ | — | — | — | 0.010 |
| $MgCl_2$ | — | — | — | 0.010 |
| Water | q.s to 100 | q.s to 100 | q.s to 100 | q.s to 100 |
| pH | 7.6 | 7.2 | 7.0 | 7.3 |
| Osmolality (mOsmo/kg) | 260 | 240 | 239 | 230 |
| Mark-Houwink constant | 1.4 | 0.9 | 1.1 | 1.2 |

Comparison of the Mark-Houwink constant revealed that a lower concentration of carboxymethylcellulose and glycerin, resulted in the stiff coil properties relating to a desired long lasting formula. Furthermore, addition of sequestering agents, buffers and tonicity adjusting agents do not diminish, and even enhances the stiff coil properties.

Example 4

Preservative Efficacy

Formulation 9 was tested for preservative efficacy. Formulation 9 passed the preservative efficacy test. To the other formulations, about 0.5 ppm alexidine or about 0.5 ppm poly (hexamethylene biguanide) is added as a preservative. The formulations with a preservative pass the preservative efficacy test.

What is claimed is:

1. A dry eye composition comprising an aqueous solution that comprises carboxy-containing polymer at a concentration from about 1 to about 1.75 percent by weight of the solution, and a single polyol at a concentration of 2, 3, or 4 percent by weight of the solution, wherein the carboxy-containing polymer has a molecular weight in a range from 90 kDa to 700 kDa, the carboxy-containing polymer comprises carboxy-containing cellulose, and the carboxy-containing polymer has a degree of substitution value in a range from 0.25 to 1, and wherein the polyol contains 2 to 6 carbon atoms.

2. The dry eye composition of claim 1, wherein the polyol contains 2 to 4 carbon atoms.

3. The dry eye composition of claim 1, wherein the polyol is glycerin.

4. The composition of claim 1, wherein the carboxy-containing polymer is carboxyethyl cellulose.

5. The composition of claim 1, wherein the polyol is selected from the group consisting of glycerin, ethylene glycol, propylene glycol, sorbitol, mannitol and monosaccharides.

* * * * *